United States Patent [19]

Lee

[11] 3,934,028

[45] Jan. 20, 1976

[54] ACNE AND PSORIASIS TREATMENT WITH RETINOIC ACID ANALOGS

[75] Inventor: Kwan-hua Lee, San Francisco, Calif.

[73] Assignee: The Regents of the University of California, Berkeley, Calif.

[22] Filed: Apr. 22, 1974

[21] Appl. No.: 463,078

[52] U.S. Cl. .............................. 424/318; 424/344
[51] Int. Cl.$^2$ ..................................... A61K 31/20
[58] Field of Search ........................... 424/318, 344

[56] References Cited
UNITED STATES PATENTS

| | | | |
|---|---|---|---|
| 3,006,939 | 10/1961 | Pommer et al. | 260/413 |
| 3,689,667 | 9/1972 | Lee | 424/318 |
| 3,729,568 | 4/1973 | Kligman | 424/318 |
| 3,882,244 | 5/1975 | Lee | 424/318 |

FOREIGN PATENTS OR APPLICATIONS

| | | | |
|---|---|---|---|
| 901,659 | 1/1962 | United Kingdom | 424/344 |
| 906,000 | 9/1962 | United Kingdom | 424/344 |

OTHER PUBLICATIONS

Stedman's Medical Dictionary, 21st Edition (1969) pp. 18 and 1432.
Chemical Abstracts (1961) 55: 7570(e).
Chemical Abstracts 56:512(d) (1962).
Chemical Abstracts 56: 8571(e) (1962).
Chemical Abstracts 56: 3915(d) (1962).
Current Therapy (1970) pp. 534–537.
Newman et al. American Perfumer and Aromatics 5/1959 pp. 44–46.
Redfearn, Arch. of Biochem. and Biophysics 91, 226–229 (1960).
Chemical Abstracts 56: 7372d (1962).

*Primary Examiner*—Norman A. Drezen
*Attorney, Agent, or Firm*—Townsend and Townsend

[57] ABSTRACT

Skin diseases resulting from abnormal metabolic processes, such as acne and psoriasis, are treated on a repetitive basis, either internally or topically, with a dermatologically sufficient amount of 11-(2',6',6'-trimethylcyclohex-1'-enyl-1')-5,9-dimethylundeca-2,4,6,8,10-pentenoic acid or its physiologically acceptable salts to reduce the inflammation. The subject acid or its salts are found to provide remission of the dermatologically diseased condition, while avoiding side effects concommitant with the use of other analogous compounds.

5 Claims, No Drawings

ACNE AND PSORIASIS TREATMENT WITH RETINOIC ACID ANALOGS

BACKGROUND OF THE INVENTION

1. Field of the Invention

A wide variety of skin diseases are characterized by abnormal metabolic processes. Two classes of these conditions are the seborrheic dermatoses—which are typified by excessive secretion or disturbed quality of sebum, abnormal intercellular cement, and oily crusts or scales—and ichthyosiform dermatoses—which are typified by dry, scaly skin, abnormal thickening of epidermis, and rapid cell turnover in the skin. Specific diseases included in these broad categories include acne vulgaris (a seborrheic dermatosis) and psoriasis (an ichthyosiform dermatosis). Both of these conditions exhibit follicular keratin plugs. Other related conditions are ichthyosis vulgaris, senile hyperkeratosis, acanthosis, Derier's disease, keratoacanthomas, congenital ichthyosiform erythroderma, zosteriform keratosis, and lamellor ichthyosis.

Because these diseases appear on the skin and are unsightly, satisfactory agents should have relatively rapid action in the remission of the condition. In addition, the reagents should not affect the skin adversely and may not be toxic at the levels employed or the manner in which it is applied. Of particular interest, is an agent which can be taken internally, acting in a systemic manner in combatting the abnormal metabolic process.

Retinoic acid is found to be active in the remission of skin conditions, but has serious side effects. The retinoic acid when applied to the skin results in irritation and peeling of the skin, which is cosmetically undesirable. Because of the irritation, there is some discouragement of the user to employ the treatment.

2. Description of the Prior Art

U.S. Pat. No. 3,689,667 discloses the subject acid for promoting wound healing. Haeck et al., Rec. Trav. Chim. 85 (3), 334–8 (1966) reports the preparation of the subject acid. Redfearn, Arch. BioChem. BioPhys. 91 226–9 (1960) reports the $C_{25}$ homologue has a curative action in the Vitamin A-deficient rat, and is converted into Vitamin A, unlike retinoic acid. U.S. Pat. No. 3,729,568 teaches the use of retinoic acid in the treatment of acne by providing for peeling.

SUMMARY OF THE INVENTION 11-(2',6',6'-Trimethylcyclohex-1'-enyl-1')-5,9-dimethylundeca-2,4,6,8,10-pentenoic acid ($C_{22}$ acid) is found to be effective, both by itself and as its physiologically acceptable salts, in treating abnormal metabolic processes of the skin. An effective amount of the $C_{22}$ acid may be applied, either topically or internally, on a repetitive basis. Usually, improvement is encountered within a week and by 3 weeks, substantial remission of the diseased condition has occurred.

The $C_{22}$ acid is beneficial in the treatment of acne and psoriasis and may be useful in conjunction with steriod therapy for psoriasis.

DESCRIPTION OF THE SPECIFIC EMBODIMENTS

Methods and compositions are provided for treating diseases resulting from abnormal metabolic processes of the skin. The methods employ treating, either internally or topically, a host suffering from a disease resulting from an abnormal metabolic process of the skin, with $C_{22}$ acid or its physiologically acceptable salts in an acceptable vehicle. The amount employed is a physiologically acceptable amount sufficient to provide significant improvement of the diseased state, when applied on a repetitive basis over a reasonable period of time: weeks or months. When employed in the resolution of psoriasis, the $C_{22}$ acid and its physiologically acceptable salts are preferably used in conjunction with steroid therapy.

The subject acid and its physiologically acceptable salts, e.g., alkali metal salts of atomic number 11 to 19 (sodium and potassium) are particularly useful in the treatment of seborrheic dermatoses and ichthyosiform dermatoses. Specific diseases coming within these classes have previously been indicated. The amounts of the $C_{22}$ acid or its salts will depend upon the manner of application and the particular disease state. In fluid compositions, such as solutions, ointments, creams and the like, the active ingredient will generally be present in from about 0.01 to 1 weight percent. In solvents or hydrophilic vehicles, the dosage level would generally be from about 0.01 to 0.5 weight percent. In lipophilic bases, the amount will generally range in from about 0.1 to 1 weight percent. When taken orally, the daily dosage, usually divided into three portions, will range from about 30 to 300mg daily, taken over from 2 to 8 weeks. For treatment of ichthyosiform dermatosis, preferably at least about 5mg daily will be taken. The tablets or capsules will usually have from about 5 to 30 weight percent of the active ingredient. Application is continued until substantial remission of the abnormal metabolic process is achieved.

Depending on the particular diseased state which is involved and the manner of application of the active material, various other materials will be used in conjunction with the active ingredient. When the active ingredient is to be taken orally, it can be provided in capsule form or as a tablet. In capsule form, it is conveniently formulated with a major amount of lactose. In tablet form, it is conveniently formulated with extenders, e.g., cellulose; lubricants, e.g., polyethylene glycol; and silica.

For hydrophilic or solvent formulations, various physiologically acceptable liquids may be employed in major amounts, normally ranging from about 80 to 99.95 weight percent. Acceptable solvents include ethanol, propylene glycol, and water. Various surfactants may be added, either individually or in combination, which will normally be present in from about 0.1 to a total of 5 weight percent of the composition. The surfactants may be non-ionic, anionic or cationic, including polyethylene glycols, their esters and ethers, alkylbenzene sulfonates, soda soaps, and the like. Physiologically acceptable thickening agents may also be added, normally in amounts of from about 0.1 to 2 weight percent, when a gel is desired. Antioxidants may be added, such as BHT and BHA, normally in minor amounts, generally from about 0.01 to 0.5 weight percent. Bacteriostatic and bactericidal agents may be added in minor amounts. Emollients may be added, such as glycerine, in amounts ranging from about 5 to 15 weight percent. Also, buffers can be added or mineral bases to provide the desired pH.

In a special situation, cotton swabs can be provided which employ the active ingredient in a vehicle such as ethanol or isopropanol in combination with propylene glycol.

The lipophilic formulations, such as anhydrous creams and ointments, will generally have a base derived from fatty alcohols, and polyethylene glycols. Additional additives will include alcohols, non-ionic surfactants, and antioxidants. For ointments, the base will normally be an oil or mixture of oil and wax, e.g., petrolatum. Also, an antioxidant will normally be included in minor amounts.

The following lists various exemplary formulations in which the $C_{22}$ acid may be formulated for either topical or oral use.

I. Oral Formulations.
Capsules

| | | mg/capsule |
|---|---|---|
| 1. | $C_{22}$ retinoic acid derivative | 50 mg |
| 2. | Lactose | 250 mg |

Gelatin capsules No. 2

Tablets

| | | mg/tablet |
|---|---|---|
| 1. | $C_{22}$ retinoic acid derivative | 25 mg |
| 2. | Sta Rx 1500 | 100 mg |
| 3. | Microcrystalline cellulose (Avicel) | 146.5 mg |
| 4. | Polyethylene glycol 6000 powder | 3 mg |
| 5. | Cab O Sil M-5 | 0.5 mg |

II. Hydrophilic or Solvent Formulations.
Liquid

| | | w/v |
|---|---|---|
| 1. | $C_{22}$ retinoic acid derivative | 0.05 g |
| 2. | 95% ethyl alcohol | 50 ml |
| 3. | Propylene glycol | 50 ml |

Gel 0.1%

| | | Grams/100.0 g w/w |
|---|---|---|
| 1. | $C_{22}$ retinoic acid derivative | 0.1 g |
| 2. | Ethyl alcohol | 10.0 |
| 3. | Tween 80 | 2.0 |
| 4. | BHT | 0.05 |
| 5. | BHA | 0.05 |
| 6. | Thimerosal | 0.01 |
| 7. | Sodium hydroxide | 0.4 |
| 8. | Versene 100 | 0.1 |
| 9. | Carbopol 940 | 1.0 |
| 10. | Water, purified | 86.29 |

Cream 0.2%

| | | Gram/100.0 g w/w |
|---|---|---|
| 1. | $C_{22}$ retinoic acid derivative | 0.2 g |
| 2. | BHT | 0.02 |
| 3. | Tween 80 | 2.0 |
| 4. | Alcohol, ethyl | 10.0 |
| 5. | Acid, stearic | 16.2 |
| 6. | Potassium carbonate | 0.9 |
| 7. | Glycerin | 8.0 |
| 8. | Propylene glycol | 5.0 |
| 9. | Water, purified | 57.5 | pH 4.5–5.0 to be adjusted with hydrochloric acid (10% solution)

Cotton Swabs

| | | w/v |
|---|---|---|
| 1. | $C_{22}$ retinoic acid derivative | 0.1 g |
| 2. | Isopropyl alcohol 99%, or Ethanol 95% | 50 ml 50 ml |
| 3. | Propylene glycol | 50 ml |

III. Lipophilic Formulations.
Cream, Anhydrous

| | | G/100 g w/w |
|---|---|---|
| 1. | $C_{22}$ retinoic acid derivative | 0.3 g |
| 2. | Ethyl alcohol | 10.0 |
| 3. | Tween 80 | 6.0 |
| 4. | BHT | 0.02 |
| 5. | Cetyl alcohol | 3.0 |
| 6. | Stearyl alcohol | 3.0 |
| 7. | Carbowax 4000 | 14.0 |
| 8. | Polyethylene glycol | 63.68 |

Ointment

| | | Grams/w/w |
|---|---|---|
| 1. | $C_{22}$ retinoic acid derivative | 0.5 g |
| 2. | BHT | 0.02 g |
| 3. | Mineral oil | 9.88 g |
| 4. | Petrolatum white | 89.61 g |

In order to demonstrate the activity of the $C_{22}$ acid, the following studies were carried out.

A group of five patients was employed, which had chronic stable psoriasis, which was more or less resistant to topical steroid therapy. Retinoic acid was compared in the study to the $C_{22}$ acid. The test agents were applied to one or two equivalently matched lesions on opposite sides thrice daily for 3 weeks. The solutions employed 0.02 weight percent of the active ingredient in a base consisting of 80% propylene glycol and 20% ethanol by volume. No other therapy was utilized.

While complete clearing was not obtained, the beneficial effects were unequivocal. At least a 50% resolution was obtained by 3 weeks with four of the five subjects. The following table indicates the comparison between retinoic acid, R, and the $C_{22}$ acid. The arrow indicates which of the two acids was superior, with the percent improvement indicated for the superior result.

Table I

| Subject | 3 Weeks | % Improvement |
|---|---|---|
| 1 | $C_{22} > R$ | 75 |
| 2 | $R > C_{22}$ | 25 |
| 3 | $C_{22} > R$ | 50 |
| 4 | $C_{22} > R$ | 50 |
| 5 | $C_{22} = R$ | 75 |

It is noteworthy that the $C_{22}$ acid is highly effective in providing resolution of the psoriatic condition. In addition, except for one resistant subject, in three of the four cases where 50% resolution or greater was obtained, the $C_{22}$ acid was better than retinoic acid. The $C_{22}$ acid was appreciably less irritating to the human skin than retinoic acid.

Oral administration of the $C_{22}$ acid was studied in the treatment of psoriasis. Several patients were given 50mg total daily dosage, in three doses, for 6 to 7 weeks. The progress of the disease was followed by physical examination and electron microscopic study of skin biopsies. Blood chemistry (12 tests), kidney function and liver function tests were run on the patients to evaluate any potential toxicity. Remission of the psoriatic condition was observed, the electron microscopic examination showing the tissue to be free from abnormal signs, and there were no side effects at the end of approximately 6 weeks.

In a study with rabbits, the effect on acne was determined. The procedure consists of applying 10% crude coal tar 5 days a week for 2 weeks to the external ear canal of young albino rabbits. This produces comedones very similar to the human variety. At the end of 2 weeks, the test agent is supplied once daily to one ear canal while the control, or the reference material is applied to the opposite ear for a period of 2 weeks. The tissue is horizontally sectioned and the reduction of comedones estimated.

Routinely, three animals are employed per test. The concentrations employed were 0.1 weight percent and 0.025 weight percent in equal parts of ethanol and propylene glycol.

At 0.1 weight percent, moderate to great decrease of comedones was observed, while at 0.025 weight percent, slight to moderate decrease of comedones was observed. In the subject test, retinoic acid showed equal or somewhat superior performance in the decrease of comedones. The $C_{22}$ acid did not produce irritation. All sites treated with retinoic acid produced marked irritation of the skin.

A number of children were treated using 0.3 weight percent of the $C_{22}$ acid in a non-ionic base. Each of the children applied, each night before retiring, a small amount of the cream on the skin where an acne condition was evident. In 3 weeks or fewer, substantial remission of the acne condition was evident. There was no evidence during the treatment of any irritation or peeling of the skin due to the use of the cream.

It is evident from the above results that the $C_{22}$ acid is extremely effective in the treatment of a wide variety of abnormal metabolic skin conditions. The $C_{22}$ acid can be employed topically or internally, and is found with internal ingestion not to have adverse effects. The $C_{22}$ acid is extremely effective in remitting psoriatic and acne conditions and can be used without having undesirable side effects, both physiological and cosmetic.

In the studies made, there was little or no evidence of any irritation of the skin or peeling. The patients did not suffer from undesirable side effects of the treatment and were encouraged by the improvement in the skin disease.

Although the foregoing invention has been described in some detail by way of illustration and example for purposes of clarity of understanding, it will be obvious that certain changes and modifications may be practiced within the scope of the appended claims.

What is claimed is:

1. A method of alleviating acne in a patient in need thereof which comprises topically administering to said patient in an amount effective for remission of said acne of 11-(2,6', 6' trimethylcyclohex-1'enyl-1')-5,9-dimethylundeca-2,4,6,8,10-pentenoic acid.

2. The method of claim 1 wherein said acid is administered as a composition comprising 0.01 to 1.0 weight per cent of said acid in admixture with a pharmaceutically acceptable carrier.

3. The method of claim 2 wherein said composition is in the form of a solution.

4. The method of claim 2 wherein said composition is in the form of an ointment.

5. The method of claim 2 wherein said composition is in the form of a gel.

* * * * *